United States Patent
Duong et al.

(10) Patent No.: US 8,474,976 B2
(45) Date of Patent: Jul. 2, 2013

(54) AUTOMATIC ACCOMMODATIVE SPECTACLES USING SENSORS AND FOCUSING ELEMENTS

(76) Inventors: Thang Duong, San Jose, CA (US); Yibin Tian, Menlo Park, CA (US)

( * ) Notice: Subject to any disclaimer, the term of this patent is extended or adjusted under 35 U.S.C. 154(b) by 227 days.

(21) Appl. No.: 12/916,508

(22) Filed: Oct. 30, 2010

(65) Prior Publication Data

US 2012/0105802 A1    May 3, 2012

(51) Int. Cl.
| | |
|---|---|
| *A61B 3/14* | (2006.01) |
| *A61B 3/00* | (2006.01) |
| *A61B 3/10* | (2006.01) |
| *G02F 1/1335* | (2006.01) |
| *G03B 21/26* | (2006.01) |

(52) U.S. Cl.
USPC ............. 351/210; 351/200; 351/205; 349/11; 353/28

(58) Field of Classification Search
USPC .................. 351/210, 168, 200, 205, 206, 41, 351/159, 7; 349/11; 345/7, 9; 353/11–12, 353/28, 119; 310/49 R, 156.32, 156.33, 156.34, 310/156.35, 266–268, 156.02; 340/438, 980, 340/995.1, 815.47, 815.74
See application file for complete search history.

(56) References Cited

U.S. PATENT DOCUMENTS

| | | | |
|---|---|---|---|
| 3,712,716 A | 1/1973 | Cornsweet et al. | |
| 3,856,381 A | 12/1974 | Hedman, Jr. et al. | |
| 3,877,798 A | 4/1975 | Tolar et al. | |
| 3,975,093 A | 8/1976 | Upton | |
| 4,287,410 A | 9/1981 | Crane et al. | |
| 4,472,036 A | 9/1984 | Kitani | |
| 4,572,616 A | 2/1986 | Kowel et al. | |
| 4,929,069 A | 5/1990 | Shibayama | |
| 4,988,183 A | 1/1991 | Kasahara et al. | |
| 4,993,825 A | 2/1991 | Abe et al. | |
| 5,231,674 A | 7/1993 | Cleveland et al. | |
| 5,430,505 A | 7/1995 | Katz | |
| 5,861,936 A * | 1/1999 | Sorensen | 351/200 |
| 5,956,183 A | 9/1999 | Epstein et al. | |
| 5,991,096 A | 11/1999 | Estelle | |
| 6,027,216 A | 2/2000 | Guyton et al. | |
| 6,283,954 B1 | 9/2001 | Yee | |
| 6,517,203 B1 | 2/2003 | Blum et al. | |
| 6,616,691 B1 | 9/2003 | Tran | |
| 7,142,369 B2 | 11/2006 | Wu et al. | |
| 7,321,469 B2 | 1/2008 | Ohno | |
| 7,382,545 B2 | 6/2008 | Jung et al. | |
| 7,466,493 B2 | 12/2008 | Kim et al. | |
| 7,522,256 B2 | 4/2009 | Horiuchi et al. | |
| 7,548,380 B2 | 6/2009 | Jeong | |
| 7,553,019 B2 | 6/2009 | Kuiper et al. | |
| 7,672,059 B2 | 3/2010 | Batchko et al. | |

(Continued)

*Primary Examiner* — Dawayne A Pinkney
(74) *Attorney, Agent, or Firm* — Chen Yoshimura LLP

(57) ABSTRACT

A pair of spectacles that can automatically change its power so that a fixation region of interest (ROI) of the user is always in focus. The automatic accommodative spectacle device includes focusing elements, sensors, line of sight detector, focus engine, focusing element controller, and power supply. The line of sight detector determines the line of sight for the left and right eyes of the user using data from the sensors. The focus engine uses the lines of sight for left and right eyes to determine the user's fixation ROI. The fixation ROI is used to determine powers for the focusing elements in order to bring the fixation ROI into focus. The focusing element controller carries out the needed optical power adjustment to apply to the focusing elements. Optional light sources may be provided.

16 Claims, 3 Drawing Sheets

U.S. PATENT DOCUMENTS

| | | |
|---|---|---|
| 7,701,642 B2 | 4/2010 | Obinata |
| 2006/0089712 A1 | 4/2006 | Malecaze |
| 2006/0119794 A1* | 6/2006 | Hillis et al. .................. 351/205 |
| 2009/0262298 A1 | 10/2009 | Chen |
| 2010/0053543 A1 | 3/2010 | Silver et al. |

* cited by examiner

AUTOMATIC ACCOMMODATIVE SPECTACLES USING SENSORS AND FOCUSING ELEMENTS

BACKGROUND OF THE INVENTION

1. Field of the Invention

This invention relates to spectacles. In particular, it relates to automatic accommodative spectacles that use sensors to determine a patient's fixation region of interest (ROI) and automatically adjust the optical power of focusing elements on the spectacles to help him/her remain focused on the fixation ROI.

2. Description of the Related Art

Spectacles and contact lenses are commonly used optical devices to correct refractive errors, such as myopia (near-sightedness) and hyperopia (farsightedness). Most prescribed spectacles and contact lenses are unifocal that have one fixed optical power. Unfortunately, patients' refractive errors can change overtime and unifocal correction devices cannot adapt to such changes. In addition, patients with presbyopia, that is, people who cannot accommodate due to aging, need different optical powers to clearly see targets at various distances. In recent years, accommodative intraocular lenses (A-IOL) have been reported, such as U.S. Pat. No. 6,616,691, US patent application 2006/0089712. But A-IOL can only be implanted in patients' eyes after cataract surgeries. A number of multifocal spectacles and contact lenses have been proposed and/or produced; they can provide either a few discrete number of optical power or continuous varying optical powers (U.S. Pat. Nos. 3,877,798, 3,975,093 and 4,472,036), which usually requires the patients to use different regions of the devices or look at targets in specific fashions, significant constraints on how patients look at their targets of interest.

A focusing element is an optical device that can vary its focusing capability. There are a number of methods to achieve variable focus. Some variable focus lenses have been proposed/produced to make spectacles (U.S. Pat. Nos. 5,956,183, 6,517,203, 7,553,019, and US patent application 2010/0053543). However, in these proposals, how to determine the needed optical power of the lenses are not specified. The amount of optical power adjustment is usually based on the feedback from visual perception. Such devices can be useful for patients in certain cases where the viewing targets are stationary or changing infrequently, but are not practical for general usage.

SUMMARY OF THE INVENTION

For patients who cannot dynamically change their lens power to focus on the fixation ROI, a pair of spectacles that can automatically change its power so that the fixation ROI is always in focus is needed.

Accordingly, the present invention is directed to a spectacle device that substantially obviates one or more of the problems due to limitations and disadvantages of the related art.

An object of the present invention is to provide a spectacle device that automatically accommodates so that the fixation ROI is always in focus.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, as embodied and broadly described, the present invention provides an automatic accommodative spectacle device for use by a user, which includes: a spectacle frame; one or more focusing elements mounted on the spectacle frame; one or more sensors located adjacent the one or more focusing elements for capturing signals about left and right eyes of the user; a line of sight detector coupled to the sensors for determining a line of sight for the left eye and a line of sight for the right eye of the user based on the signals captured by the sensors; a focus engine coupled to the line of sight detector for determining a fixation region of interest of the user based on the lines of sight for the left and right eyes, and for determining optimum powers for the focusing elements based on the fixation region of interest; and a focusing elements controller connected to the focusing elements and the focus engine for controlling optical powers of the focusing elements based on the optimum powers for the focusing elements determined by the focus engine.

The focus engine determines fixation region of interest by minimizing the distance between the two lines of sight or using a pre-loaded look up table that may be updated as needed. A calibration procedure to generate the lookup table may be done on a per-patient basis or on a population basis.

The automatic accommodative spectacle device further includes a power supply for supplying power to the focusing elements, the sensors, the line of sight detector, the focus engine and the focusing elements controller.

The device may also include an optional light source, which may be turned on or off as needed.

In another aspect, the present invention provides a method for focusing an automatic accommodative spectacle device for use by a user, which includes: capturing signals about left and right eyes of the user by one or more sensors; determining a line of sight for the left eye and a line of sight for the right eye of the user by a line of sight detector based on the signals captured by the sensors; determining a fixation region of interest of the user by a focus engine based on the lines of sight for the left and right eyes; determining optimum powers for the focusing elements by the focus engine based on the fixation region of interest; and controlling optical powers of one or more focusing elements of the automatic accommodative spectacle device by a focusing elements controller based on the optimum powers for the focusing elements determined by the focus engine.

It is to be understood that both the foregoing general description and the following detailed description are exemplary and explanatory and are intended to provide further explanation of the invention as claimed.

DETAILED DESCRIPTION OF THE PREFERRED EMBODIMENTS

Figure 1:
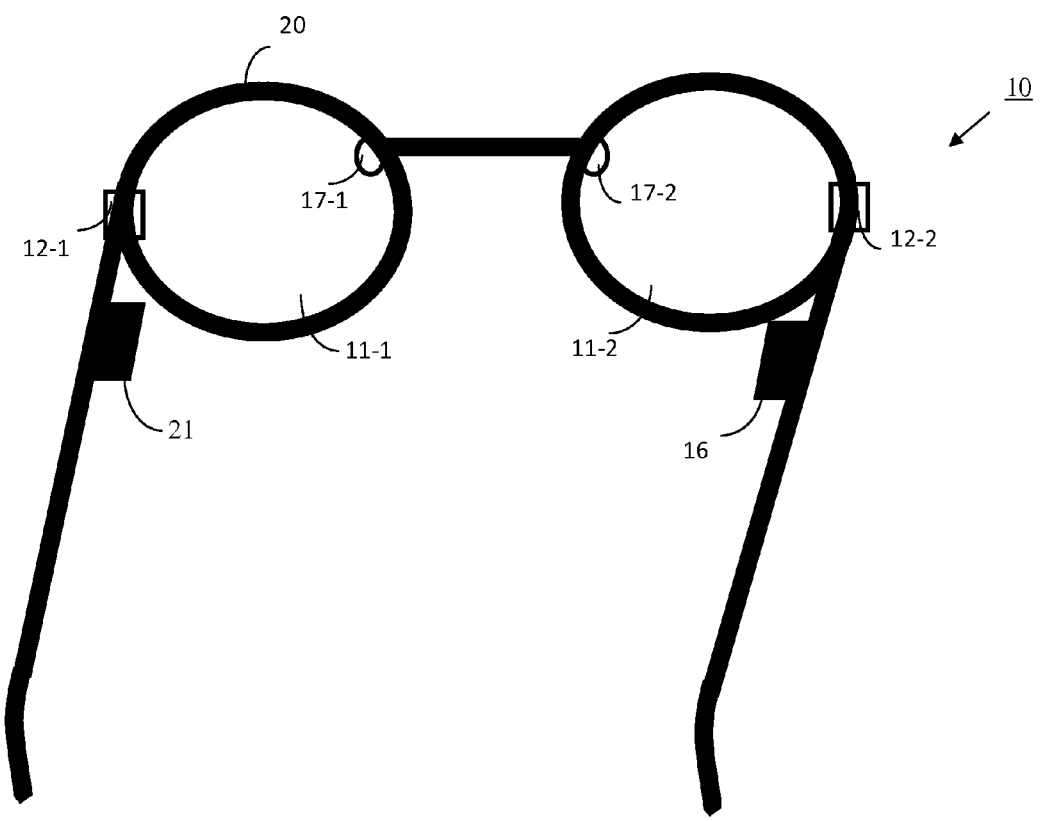
FIG. 1 schematically illustrates a pair of automatic accommodative spectacles according to an embodiment of the present invention.
Figure 2:
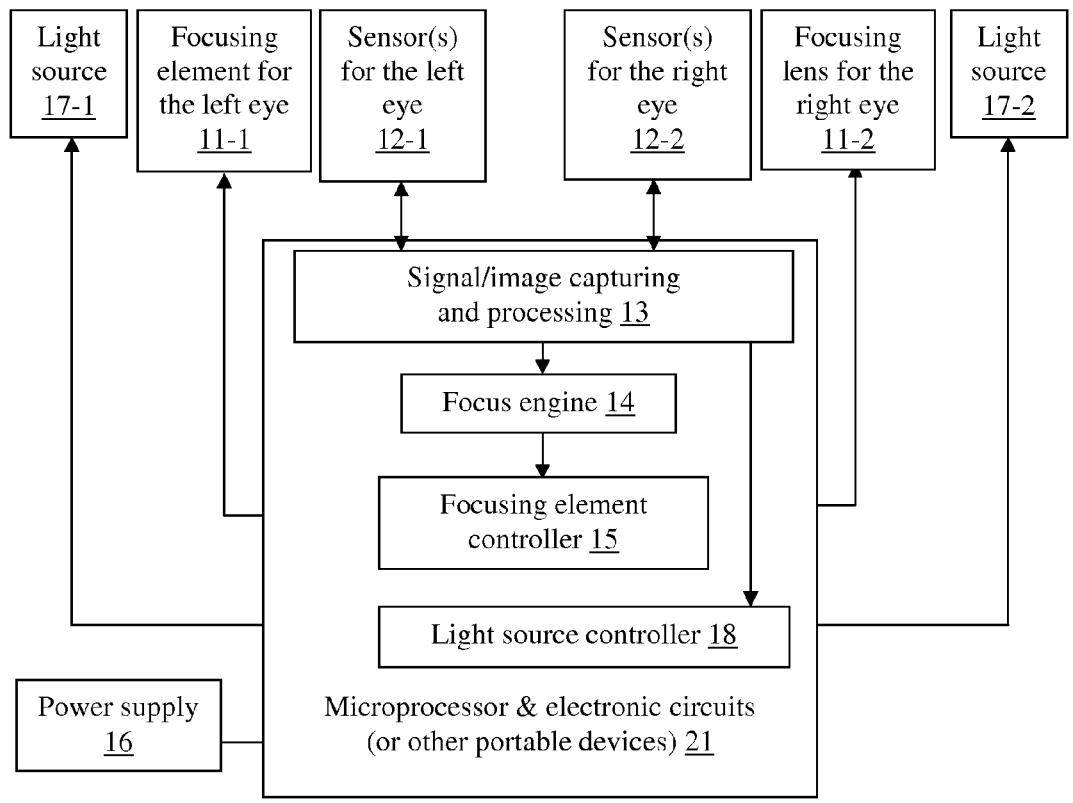
FIG. 2 is a block diagram illustrating components of the automatic accommodative spectacles according to an embodiment of the present invention.

This disclosure describes a spectacle device that automatically focuses to the fixation ROI of the patient (user). As shown in FIGS. 1 and 2, the spectacle device 10 includes left and right focusing elements 11-1 and 11-2, left and right sensors 12-1 and 12-2, a signal or image capturing and processing section (also referred to as the line of sight detector) 13, a focus engine 14, a focusing element controller 15, and a power supply 16. Optionally, the spectacle device also includes left and right light sources 17-1 and 17-2, and a light source controller 18 for controlling the light sources.

As shown in FIG. 1, these various components are attached to a spectacle frame 20. The number and locations of various components shown in FIG. 1 are for illustration only. Actual implementation may vary.

The line of sight detector 13, focus engine 14, focusing element controller 15, and optional light source controller 18 may be implemented in a control unit 21, which may include microprocessor(s) executing software programs, and/or electronic circuits such as ASIC and FPGA. The control unit 21 may be a dedicated unit mounted on the frame 20, or it may be located on a separate, dedicated portable device not mounted to the frame 20. Alternatively, the components 13, 14, 15 and 18 may be implemented as a part of another (not-dedicated) portable device, such as a PDA (personal digital assistant), a mobile phone, a music player, a GPS device, and so on. The components 13, 14, 15 and 18 may also be located in a distributed manner, i.e., some mounted on the frame 20 and some located on a separate portable device.

Figure 3:
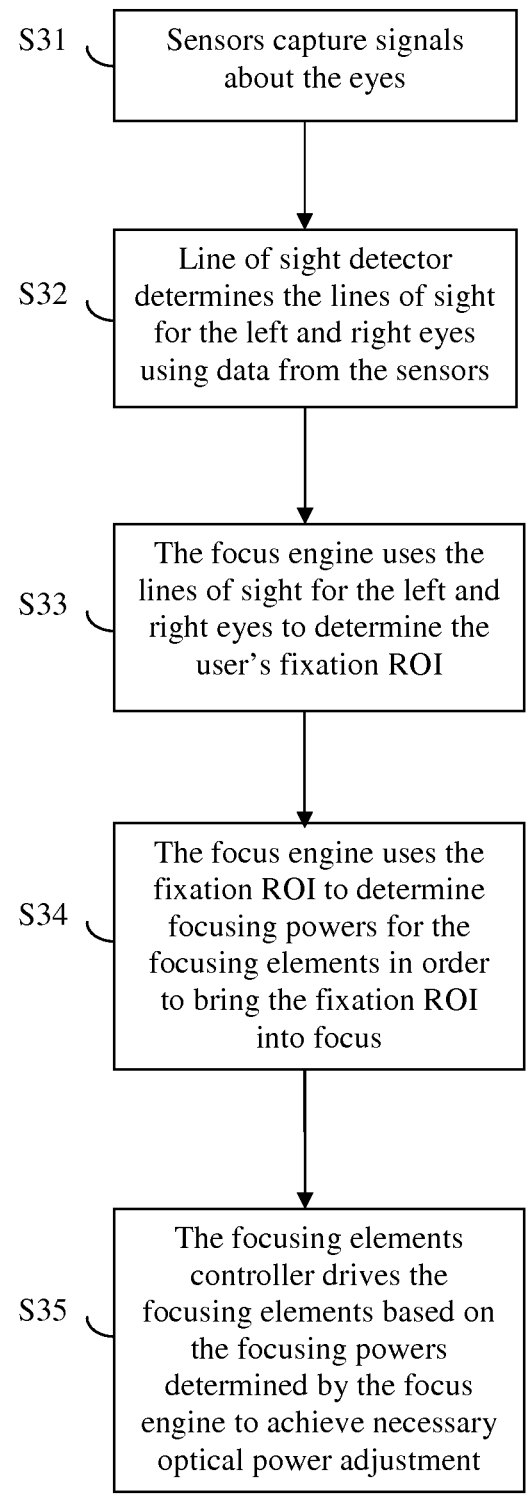
FIG. 3 is a flow chart showing the operation of the automatic accommodative spectacles according to an embodiment of the present invention.

The functions and operations of the various components are described with reference to FIG. 3.

The sensors 12-1 and 12-2 capture signals about the user's eyes (with or without the light sources) (step S31). For example, the sensors may be image sensors used to image the eye, i.e., the captured signals are one or more images of each eye. There may be one or more sensors for each eye. The optional light sources 17-1 and 17-2 shine light on the user's eyes and improve signal to noise ratio of the signals/images measured by the sensors. Preferably, the light sources 17-1 and 17-2 are turned on and off to control power usage and improve sensor signal-to-noise ratio. For example, the light sources 17-1 and 17-2 may be turned on when ambient light level is low and off when it is high, and it may be turned off when the batter is low. Preferably, the light sources 17-1 and 17-2 are only turned on when the sensors indicate that the natural light illumination is not sufficient for the sensor to adequately sense the signals about the eyes. There may be zero or more light sources 17-1 and 17-2 for each eye.

The line of sight detector 13 determines the lines of sight for the left and right eyes using data from the sensors 12-1 and 12-2 (step S32). The focus engine 14 uses the lines of sight for the left and right eyes to determine the user's fixation ROI (step S33). Further, it uses the fixation ROI to determine focusing powers for the focusing elements in order to bring the fixation ROI into focus for the user (step S34). Based on the focusing powers determined by the focus engine 14, the controller 15 drives the focusing elements 11-1 and 11-2 to achieve necessary optical power adjustment (step S35).

Steps S31 to S35 are repeated, preferably repeated constantly, unless instructed not to do so.

The line of sight detector 13 and the sensors 12-1 and 12-2 may use any appropriate methods to determine the line of sight of each eye. Various known methods exist to perform this function. One common method utilizes one or two dimensional photo-detectors to image the eyeball. Image processing is performed on the images to determine the line of sight of the eye. This method is described in U.S. Pat. Nos. 5,231,674, 6,283,954, 3,712,716, 4,988,183, 4,993,825, and 4,287,410. Other, less commonly used, methods also exist to perform the same function with various trade-offs. For example, U.S. Pat. No. 5,430,505 uses an array of light sources and corresponding light detection devices, and U.S. Pat. No. 6,027,216 uses scleral search coil to determine the line of sight. One skilled in the art will be able to implement the sensors 12-1 and 12-2 and the light of sight detector 13 based on the teaching of these references, or use other devices and methods currently known or will be developed in the future. The scope of this invention encompasses any suitable implementation of the line of sight detector 13 and the sensors 12-1 and 12-2.

The focusing elements 11-1 and 11-2 are optical devices that can vary their focusing power. They may be variable focus lenses or other focusing devices, such as phase plates. There are a number of known methods to achieve variable focus. One common method utilizes multiple-element composite lenses that can adjust the distance between two or more optical elements, as described in U.S. Pat. Nos. 4,929,069, 5,991,096, 7,321,469, 7,548,380, etc. A second method utilizes liquid crystal devices, the optical transmission properties of which can be controlled electrically, as described in U.S. Pat. Nos. 3,856,381, 4,572,616, 7,522,256, U.S. Patent Application Publication 20090262298, etc. A third method uses enclosed liquid, the surface curvature of which can be modified electrically or mechanically, as described in U.S. Pat. Nos. 7,142,369, 7,382,545, 7,466,493, 7,672,059, 7,701,642, etc. One skilled in the art will be able to implement the focusing elements 11-1 and 11-2 and the focusing element controller 15 based on the teaching of these references, or use other devices and methods currently known or will be developed in the future. The scope of this invention encompasses any suitable implementation of the focusing elements 11-1 and 11-2 and the focusing element controller 15.

The focusing elements 11-1 and 11-2 can be controlled by any appropriate method. For example, the focusing elements may be controlled directly by electrical signals from the focusing element controller 15, or, alternatively, the focusing elements are controlled by motorized mechanical, solid state, or MEMS elements, which in turn are electrically controlled by focusing element controller 15. In both cases, the current status of the focusing elements may be reported to and used by the focusing element controller 15 to determine the proper control signals to be delivered.

A pair of focusing elements 11-1 and 11-2 are needed, one for the left eye, and the other for the right eye. In a preferred embodiment, the two focusing elements 11-1 and 11-2 are controlled independently to achieve different amount of optical power for the two eyes. Alternatively, they can also be adjusted in the same amount if desired. The focusing elements 11-1 and 11-2 may be enclosed directly within the spectacle frame 20, or have their own supporting structures that fit into the spectacle frame.

As stated earlier, lines of sight of the left and right eyes are combined to determine the ROI. This can be done in various ways. One of such method is described here. Suppose the line of sights parameterized with respect to t are given by the equations:

$$l(t) = \begin{bmatrix} l_1(t) \\ l_2(t) \\ l_3(t) \end{bmatrix} = \begin{bmatrix} a_1 \\ a_2 \\ a_3 \end{bmatrix} t + \begin{bmatrix} b_1 \\ b_2 \\ b_3 \end{bmatrix}$$

for the left eye and $$r(t) = \begin{bmatrix} r_1(t) \\ r_2(t) \\ r_3(t) \end{bmatrix} = \begin{bmatrix} c_1 \\ c_2 \\ c_3 \end{bmatrix} t + \begin{bmatrix} d_1 \\ d_2 \\ d_3 \end{bmatrix}$$

for the right eye. For these equations, axis 1 and axis 2 span coronal plane and axis 3 is perpendicular to the coronal plane. For axis 3, positive faces forward along the gaze direction, and coordinate 0 is defined to be the position of the lens nodal points projected onto axis 3. Distances on all axes are in meters. Parameters $a=(a_1,a_2,a_3)$, $b=(b_1,b_2,b_3)$ for the left eye and $c=(c_1,c_2,c_3)$, $d=(d_1,d_2,d_3)$ for the right eye are determined from eye trackers on the left and right eyes, respectively. The fixation plane can be computed by first solving the following equation:

$$(t_1^*, t_2^*) = \operatorname*{argmin}_{t_1,t_2} \sum_{j=1}^{3} (a_j t_1 - c_j t_1 + b_j - d_j)^2$$

and the ROI is given by ROI=r* where r* is any point between $(a_1 t_1^*+b_1, a_2 t_1^*+b_2, a_3 t_1^*+b_3)$ and $(c_1 t_2^*+d_1, c_2 t_2^*+d_2, c_3 t_2^*+d_3)$. In particular, the coordinate of the fixation plane is given by z=z* where z* is any point between $a_3 t_1^*$ and $c_3 t_2$.

The solution to this equation is given by $$t_2^* = \frac{\langle c, b-d \rangle \|a\|^2 + \langle a, c \rangle \langle a, d-b \rangle}{\|a \times c\|^2}$$

$$t_1^* = \frac{\langle a, d-b \rangle + \langle a, c \rangle t_2^*}{\|a\|^2}$$

where $\langle \cdot \rangle$, $\times$, and $\|\cdot\|$ denote the inner product, cross product, and norm-2 operators, respectively. For vectors $x=(x_1,x_2,x_3)$ and $y=(y_1,y_2,y_3)$, these operators are defined as:

$$\langle x, y \rangle = x_1 y_1 + x_2 y_2 + x_3 y_3$$

$$x \times y = (x_2 y_3 - x_3 y_2, x_3 y_1 - x_1 y_3, x_1 y_2 - x_2 y_1)$$

$$\|x\| = \langle x, x \rangle = x_1^2 + x_2^2 + x_3^2$$

If the lines of sight are not parallel and intersect at a fixation plane in front of the patient, then $\|a \times c\|^2$ is always nonzero and the value z* is always positive.

Once the ROI is determined, the controllers adjust focusing elements so that the fixation ROI becomes clear. One such method is by adjusting the dioptric power of the left and right to $$D_{left} = \frac{1}{z^*} + C_{left} \text{ and } D_{right} = \frac{1}{z^*} + C_{right},$$

respectively. Here, $C_{left}$ and $C_{right}$ are correction powers required so that the left and right eyes focus at infinity. Other optical power adjustment schemes can be utilized as well.

Alternatively, the device can be calibrated for individual patients, and a look-up-table (LUT) can be used to relate the lines of sight of the two eyes to the appropriate optical power of the two focusing elements.

Preferably, the needed optical power adjustment resolution should be higher for near-distance fixation ROI, and lower for far-distance fixation ROI. The optical power adjustment resolution transition can be nonlinear from near-distance to far-distance. Approximations can be utilized to reduce the computation and/or the size of look-up-table as described above. The focus power look up table can be generated by a calibration procedure, by averaging data over population or on a per-patient basis.

On a per-patient basis, the patient is asked to look at an image positioned at various points in the visual field. The patient is also asked to adjust the power of the lens until such image becomes clear. This power is entered into the look up table as a corresponding power for that position in the visual field. The look up table defines a correspondence between spatial position in the visual field and optical power. This look up table may be updated as needed.

For data generated over a population, data generated from the per-patient basis procedure would be averaged for all patients with similar characteristics. For example, data for patients in the same age range would be averaged to create a lookup table for that age range. Other variables may be used as a basis for grouping patients and averaging.

The various components of the spectacle device are powered by the power source 16. Power is needed for the microprocessor & electronic circuits, the focusing elements and their controller, the sensors, and the optional light sources and their controller. The power supply 16 may be conventional batteries (rechargeable or non-rechargeable), solar energy harvesting device(s), other portable devices, or a combination of such devices. The power supply 16 may be mounted on the frame 20 or located on a separate portable device. The power supply may be the power supply of a non-dedicated portable device such as a PDA, mobile phone, etc. The power supply may also be a converter directly connecting to an electrical outlet.

It will be apparent to those skilled in the art that various modification and variations can be made in the automatic accommodative spectacle of the present invention without departing from the spirit or scope of the invention. Thus, it is intended that the present invention cover modifications and variations that come within the scope of the appended claims and their equivalents.

What is claimed is:

1. An automatic accommodative spectacle device for use by a user, comprising:
    a spectacle frame;
    one or more focusing elements mounted on the spectacle frame;
    one or more sensors located adjacent the one or more focusing elements for capturing signals about left and right eyes of the user;
    a line of sight detector coupled to the sensors for determining a line of sight for the left eye and a line of sight for the right eye of the user based on the signals captured by the sensors;
    a focus engine coupled to the line of sight detector for determining a fixation region of interest of the user by minimizing a distance between the lines of sight for the left and right eyes, and for determining optimum powers for the focusing elements based on the fixation region of interest; and
    a focusing elements controller connected to the focusing elements and the focus engine for controlling optical powers of the focusing elements based on the optimum powers for the focusing elements determined by the focus engine.

2. The automatic accommodative spectacle device of claim 1, further comprising one or more light sources for shining a light on the user's eyes.

3. The automatic accommodative spectacle device of claim 2, further comprising one or more light source controllers for controlling the one or more light sources.

4. The automatic accommodative spectacle device of claim 1, further comprising a power supply for supplying power to the focusing elements, the sensors, the line of sight detector, the focus engine, and the focusing elements controller.

5. The automatic accommodative spectacle device of claim 1, wherein the focus engine determines the fixation region of interest by using a pre-loaded look up table.

6. The automatic accommodative spectacle device of claim 5, wherein the look up table is determined on a per-patient basis or on a population basis.

7. The automatic accommodative spectacle device of claim 1, wherein the line of sight detector, the focus engine, and the focusing element controller, are implemented in a control unit, wherein the control unit includes a microprocessor executing software programs, or electronic circuits including ASIC or FPGA.

8. The automatic accommodative spectacle device of claim 7, wherein the control unit is either a dedicated unit mounted on the spectacle frame, or located on a separate portable device.

9. The automatic accommodative spectacle device of claim 1, wherein the line of sight detector utilizes one or two dimensional photo-detectors to image eyeballs of the user.

10. The automatic accommodative spectacle device of claim 1, wherein the focusing elements are variable focus lenses or phase plates.

11. A method for focusing an automatic accommodative spectacle device for use by a user, comprising:
   capturing signals about left and right eyes of the user by at least two sensors;
   determining a line of sight for the left eye and a line of sight for the right eye of the user by a line of sight detector based on the signals captured by the sensors;
   determining a fixation region of interest of the user by a focus engine by minimizing a distance between the lines of sight for the left and right eyes;
   determining optimum powers for the focusing elements by the focus engine based on the fixation region of interest; and
   controlling optical powers of two one or more focusing elements of the automatic accommodative spectacle device by a focusing elements controller based on the optimum powers for the focusing elements determined by the focus engine.

12. The method of claim 11, further comprising:
   shining a light on the user's eyes using one or more light sources.

13. The method of claim 12, further comprising:
   controlling the one or more light sources by one or more light source controllers.

14. The method of claim 11, wherein the focus engine determines the fixation region of interest by using a pre-loaded look up table.

15. The method of claim 14, wherein the look up table is determined on a per-patient basis or on a population basis.

16. The method of claim 11, wherein the line of sight detector utilizes one or two dimensional photo-detectors to image eyeballs of the user.

* * * * *